Aug. 26, 1947. J. T. HILDEBRANDT Plant Pat. 755
ROSE PLANT
Filed June 19, 1946
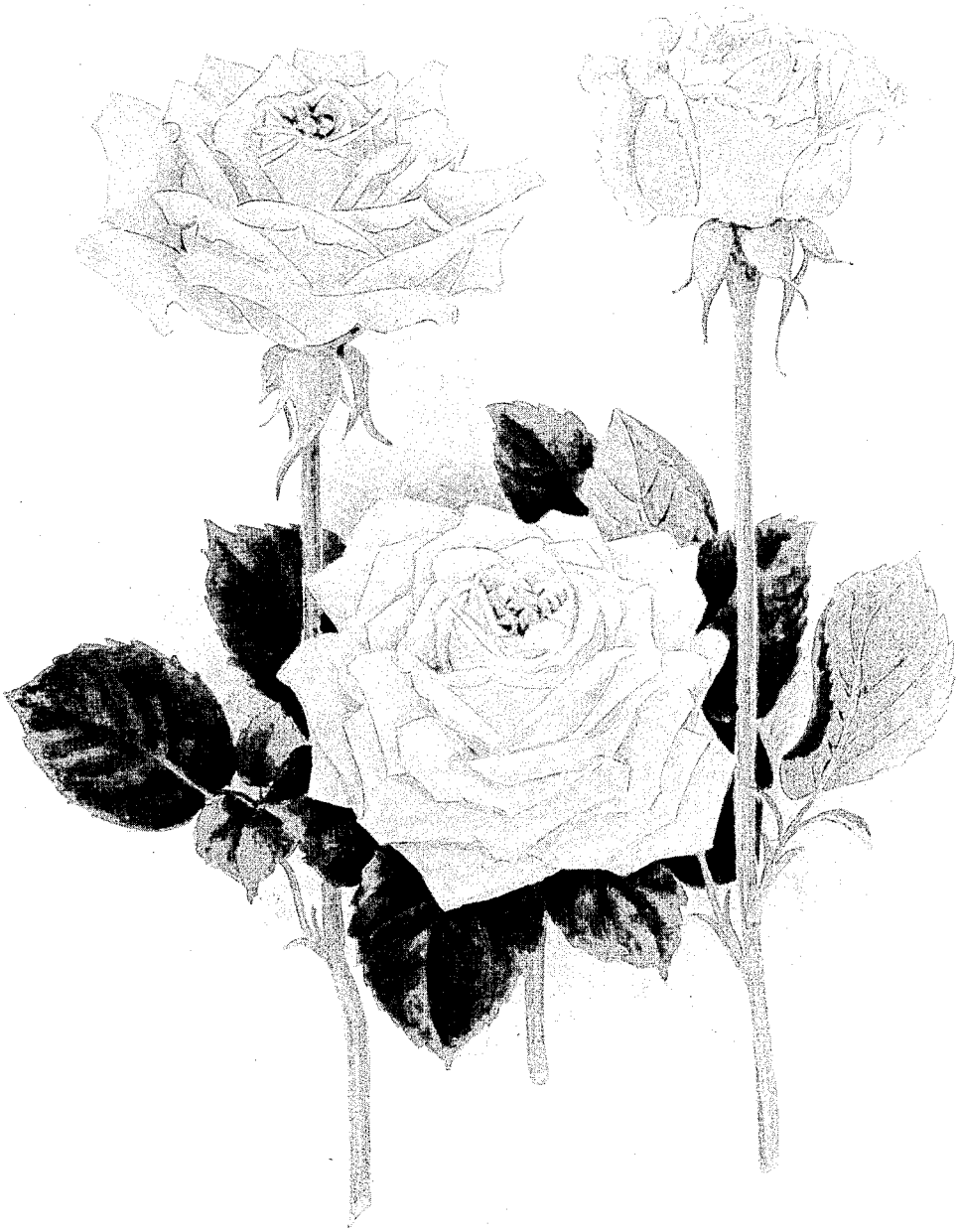
WITNESS
Addison J. Avery
INVENTOR
JOHN T. HILDEBRANDT,
Rummler Rummler & Davis,
ATTYS.

Patented Aug. 26, 1947

Plant Pat. 755

UNITED STATES PATENT OFFICE

755

ROSE PLANT

John T. Hildebrandt, Melrose Park, Ill., assignor to Albert F. Amling Co., Maywood, Ill., a corporation of Illinois Application June 19, 1946, Serial No. 677,652

1 Claim. (Cl. 47—61)

My present discovery is a new and distinct variety of rose plant, herein described and illustrated. It is a cross between "Matchless" and an unnamed seedling which resulted from repeated crossings carried on by myself and my associates since 1936 on "Talisman" for sturdy stems. This new variety has been asexually reproduced by cuttings and its characteristics appear to be permanently fixed. At the present time there are 200 plants of this variety in greenhouses at Maywood, Illinois.

The novelty of this new variety resides primarily in the dark red-purple coloring of the blooms, its American Beauty fragrance, and its unusually thick, stiff flower stems.

The accompanying illustration shows in full color specimen blooms of this new variety in various stages of development, and of approximately its natural size.

Referring to the novel characteristics of this new variety, the flower is a large, very double blossom of rich dark red coloring. The petals are numerous and tightly packed in the middle area of the open bloom, completely hiding the sexual organs. In the full open flower, the outer whorls of petals are characterized by having marginal portions thereof curled outward and downward on chordal lines at an angle to each other, but the central area remains compact.

The bud is cup-shaped, broad, short and rather flat at its top and bottom; and is very compact in its early stages of opening. There are the usual five sepals which turn downward as the bud opens and hang close to its stem.

The foliage is luxuriant and of a dark yellow-green in coloring.

An outstanding characteristic of this new rose is the persistence of its petals in hanging on until they dry. A bloom which has been kept in a vase for three weeks remains intact with none of its petals fallen. The dried rose has shrunk to about one-fourth its original size; the petals have not "blued" but the intense Tyrian rose color has turned into a dark purplish red color, which is still pleasing to the eye.

A distinguishing novelty of the final stage of this rose is the nesting arrangement of the central mass of petals into five compact radial groups. As the rose dries the outer layers of the petals curl back closer to the stem and the central mass of petals divides into five distinct, almost symmetrically nested, multi-layered batches radiating from the now exposed mass of yellow stamens and anthers. This is the only period in its development in which the stamens are conspicuous.

This new variety of rose resembles most the "Francis Scott Key" variety. The petals curl back like the "Francis Scott Key" rose; its full bud is like "Francis Scott Key" or "Matchless"; it has robust, stiff stems; the bud is short and flat like "Templar" and its fragrance is like that of the "American Beauty" rose. It is a thriving rose plant with a vigorous constitution and its blooms can be cut throughout the year in greenhouse plantings.

The following is an itemized description in schedule form of the new variety:

Parentage: Seedling.
- *Seed parent.*—"Matchless."
- *Pollen parent.*—Unknown seedling.

Blooming habit: Recurrent.

Bud:
- *Size.*—Medium.
- *Form.*—Cup-shaped, flat.
- *Sepals.*—5; do not hood over bud.

Bloom:
- *Size.*—3½ inches in diameter and 1¾ inches in depth.
- *Borne.*—Singly.
- *Stems.*—Very strong; length, 20 to 24 inches.
- *Petalage.*—50 to 100; average about 75.
- *Discoloration.*—The color has a tendency to get very dark, almost black, as the flower opens.
- *Texture.*—Satiny.
- *Affected by wet or hot weather.*—No.
- *Persistence.*—Hang on and dry.
- *Fragrance.*—Very fragrant, like "American Beauty."
- *Disease resistant.*—Yes.
- *Lasting quality.*—Very long.

Foliage: Luxuriant.

Thorns: Average number.

The color designations according to Ridgway Color Standards and Color Nomenclature are as follows:

| Section | Color | Plate |
|---|---|---|
| Main body of flower | Tyrian Rose | XII |
| Shading into | Rose Red | XII |
| Light areas at edge and high lights appear between— | Rhodamine Purple and Tyrian Rose. | XII |
| Deepest shadow tones | Pomegranate Purple | XII |
| Round areas of outside petals reflect from inner surface of adjoining petals— | Rose Red | XII |
| Main leaf color | Dark dull Yellow-Green. | XXXII |
| Under side of leaf | Mytho Green | XLI |
| Inside of calyx | Light Grape Green and Mytho Green. | XLI |
| Stem | Lettuce Green | V |

3

The Tyrian Rose coloring and fragrance of the bloom; compactness of the petals; the large size of the bloom; superior keeping qualities; abundance of foliage; stout, erect, robust flower stems; and resistance to the usual diseases prevalent among roses, make this new variety stand out as a distinctive commercial product.

I claim:

4

A new and distinct variety of rose plant, substantially as described, being characterized by the rich Tyrian Rose coloring of its flowers; their fragrance; their abundant double petalage; superior keeping qualities; their stiff, stout stems; and its continuous and free blooming habit and luxuriant foliage.

JOHN T. HILDEBRANDT.